United States Patent [19]

Bull et al.

[11] Patent Number: 5,981,554
[45] Date of Patent: Nov. 9, 1999

[54] METHOD OF TREATMENT OF SUGAR PLANT TO IMPROVE THE SUGAR CONTENT

[75] Inventors: Richard McLean Bull; Michael John Strano, both of Pinkenba, Australia

[73] Assignee: Rhone-Poulenc Agrochimie, Lyons, France

[21] Appl. No.: 08/870,488

[22] Filed: Jun. 6, 1997

[30] Foreign Application Priority Data

Jun. 7, 1996 [AU] Australia ................................ 55849/96

[51] Int. Cl.⁶ .............................. A01N 43/40; A01N 43/56
[52] U.S. Cl. ......................... 514/341; 514/403; 514/406; 514/407
[58] Field of Search .................... 514/341, 407, 514/403, 406

[56] References Cited

U.S. PATENT DOCUMENTS 5,232,940  8/1993  Hatton et al. ........................... 514/407
5,236,938  8/1993  Huang et al. ........................... 514/341

FOREIGN PATENT DOCUMENTS 0295117  12/1988  European Pat. Off. .
0385809  9/1990   European Pat. Off. .
0403300  12/1990  European Pat. Off. .
0679650  11/1995  European Pat. Off. .
19511269 10/1995  Germany .
87/03781  7/1987  WIPO .
93/06089  4/1993  WIPO .
94/21606  9/1994  WIPO .

OTHER PUBLICATIONS

*Chemical Abstracts*, 108:147200 (1987).
*Chemical Abstracts*, 72:9957 (1966).
Gaulliard, Fipronil: An insecticide, Rhone–Poulenc Argo France, Fr., Phytoma (1996), 488, 59–61.
"Le Fipronil, Insecticide à large spectre", *Phytoma—La Defense des Végétaux*, No. 488, Nov. 1996, J. Gaulliard, pp. 59–61.

*Primary Examiner*—S. Mark Clardy
*Assistant Examiner*—Alton Pryor
*Attorney, Agent, or Firm*—Burns, Doane, Swecker & Mathis, L.L.P.

[57] ABSTRACT

A method for improving and/or increasing the sugar content and/or preventing reduction of the sugar content of sugar plants, preferably sugar cane, which comprises treating said plants with an effective amount of a 1-arylpyrazole compound of the formula

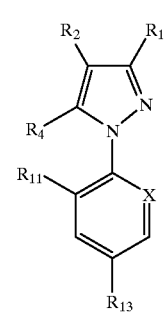

(I)

wherein the structural variables are as defined in the specification.

13 Claims, No Drawings

METHOD OF TREATMENT OF SUGAR PLANT TO IMPROVE THE SUGAR CONTENT

The invention relates to a method of treatment of sugar plants, especially sugar cane, in order to improve the sugar content of these plants.

Sugar is produced from various plants, and more particularly from sugar beet and sugar cane. Even if the growing of the sugar plants is going properly and healthy plants are obtained, the sugar content remains a permanent concern of growers.

The sugar content may vary for various reasons which are not always totally known and the nature of the variations may also be very different.

Certain pests, including insect pests may have some influence. Sugar cane weevil borer is a pest which in some respect seems to be somewhat related with the sugar production. But no really active treatment is known to control such pest and no satisfactory chemical has been identified for this weevil. Furthermore it is deemed that the content of sugar or the damaging of this content are influenced by more than one factor and/or pest. Rather, it seems that a combination of several insect pests as well as fungi or other factors might contribute to this problem.

The nature of sugar content variation may also vary substantially. It might be a quantitative variation as well as a qualitative variation. For example, the content of some specific sugars or oses, e.g. hexoses such as glucose, mannose, fructose, etc . . . may be decreased up to a point to render the sugar inappropriate for normal uses. The content of such sugars may also influence the processing of the sugar, especially the refining.

An object of the instant invention is to render sugar plants, especially sugar cane, having an improved sugar production.

Another object of the instant invention is to improve the sugar content of sugar plants, especially sugar cane.

Another object of the instant invention is to increase the sugar content of sugar plants, especially sugar cane, and/or at least to prevent reduction of sugar content.

Another object of the instant invention is to decrease (or to prevent the production of) the dextran content of sugar juices extracted from sugar plants, especially sugar cane. This dextran indeed is creating trouble in sugar refining because of its liquid character which affects the normal and/or proper crystallisation of sucrose.

Another object of the instant invention is to protect or maintain the sugar content of sugar plants, especially sugar cane, when this content is going to decrease or expected to be able to decrease.

Another object of the instant invention is to prevent the production of dextran in sugar juices extracted from sugar plants, when this content of dextran is going to increase or expected to be able to increase.

Another object of the instant invention is to provide a method which is able to control the pests which might have an influence on the sugar content of sugar plants, especially sugar cane.

Another object of the instant invention is to provide a method which is able to control the pests which might have an influence on the sugar content of sugar plants, especially the pests such as the weevil borer(s) (*Rhabdoscelus obscurus*). Other pests such as the stem borers may create similar problems. The invention is designed to control these pests too, even though the proper control of *Rhabdoscelus obscurus* is most difficult and no proper treatment is yet known.

Another object of the instant invention is to provide a sugar effective treatment of sugar plants, especially sugar cane, which is not phytotoxic to the sugar plants.

It has now been found that these objects may be partially or totally reached by mean of the instant invention.

It has now been found that these objectives can be met partially or totally by means of the methods of treatment or control as described in the instant specification.

This invention provides a method of improving and/or increasing the sugar content and/or preventing the reduction of sugar content of sugar plants, preferably sugar cane, which comprises treating the plants with an effective amount of compound of formula (I) which is hereafter defined.

This invention is also directed to a method of control of pests which might be able to affect the sugar content of sugar plants.

This invention is also directed to a method of control of sugar cane weevil borer infesting sugar plants or expected to infest sugar plants which comprises applying an effective amount of a compound of formula (I) to the locus where the insects are or are expected to be. By the word insects in the instant specification, all stages of development of the said insects are contemplated, including the larvae.

The application of active ingredient of formula (I) to the sugar plants according to the methods as here above described is preferably done by application of the said active ingredient to the stalk of the plant.

A more specific feature of the instant invention is to apply the said active ingredient to the said stalk when it comprises one to 5 nodes. Generally, one or two applications of the active ingredient are sufficient. When two applications are made, it is preferred that the first is made on a plant having one node and the last application is made upon a plant having four or five nodes.

The precise effective amount of compound of formula (I) which is applied may vary rather much, according to the intensity of infestation by pests or according to the specific species or conditions or according to the variation of sugar which is going to happen or which is expected to happen.

The effective amounts of active ingredient which are used in the invention are generally in the range from 10 to 200 g/ha, preferably 20 to 150 g/ha, and most preferably in the range from 20 to 100 g/ha.

The said application is generally made by spraying or coating or painting. Spraying is most preferred. The formulation being used for said application is advantageously a liquid formulation. Such formulations of compounds of formula (I) may be of all kinds, provided that the said compound is evenly distributed in the material. Such formulations are known, including in patent applications WO 87/3781, 93/6089, 94/21606, and European patent application EP 295,117.

In the instant invention, the formula (I) is the following:

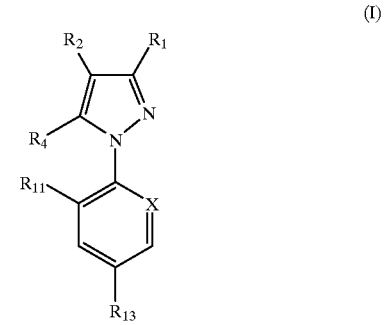

in which:

$R_1$ is CN or methyl;

$R_2$ is $S(O)_n R_3$;

$R_3$ is alkyl or haloalkyl;

$R_4$ represents a hydrogen or halogen atom or a member of the group consisting of $NR_5R_6$, $S(O)_mR_7$, $C(O)R_7$, $C(O)O\text{—}R_7$, alkyl, haloalkyl, $OR_8$ and $\text{—}N=C(R_9)(R_{10})$;

$R_5$ and $R_6$ independently represent the hydrogen atom or an alkyl, haloalkyl, C(O)alkyl, alkoxycarbonyl or $S(O)_rCF_3$ radical; or $R_5$ and $R_6$ together form a divalent alkylene radical which can be interrupted by one or two divalent heteroatoms, such as oxygen or sulfur;

$R_7$ represents an alkyl or haloalkyl radical;

$R_8$ represents an alkyl or haloalkyl radical or a hydrogen atom;

$R_9$ represents an alkyl radical or hydrogen atom;

$R_{10}$ represents a phenyl or heteroaryl group which is unsubstituted or substituted by one or more halogen atoms or a member of the group consisting of OH, —O-alkyl, —S-alkyl, cyano, and alkyl;

X represents a trivalent nitrogen atom or a $C\text{—}R_{12}$ radical, the other three valences of the carbon atom forming part of the aromatic ring;

$R_{11}$ and $R_{12}$ represent, independently of one another, a hydrogen or halogen atom;

$R_{13}$ represents a halogen atom or a haloalkyl, haloalkoxy, $S(O)_qCF_3$ or $SF_5$ group;

m, n, q, and r represent, independently of one another, an integer equal to 0, 1, or 2;

provided that, when $R_1$ is methyl, then $R_3$ is haloalkyl, $R_4$ is $NH_2$, $R_{11}$ is Cl, $R_{13}$ is $CF_3$ and X is N.

Alkyl and haloalkyl and alkoxy and haloalkoxy radicals in the definition of formula (I) generally contain from 1 to 6 carbon atoms. Similarly, the alkyl portion of the C(O)alkyl radicals and the alkoxy portion of the alkoxycarbonyl radicals generally contain from 1 to 6 carbon atoms. When $R_5$ and $R_6$ together with the nitrogen atom to which they are attached form a ring, the ring is generally 5- or 6-membered. Example of heteroaryl for $R_{10}$ is for instance pyridyl, e.g. 2-pyridyl.

A preferred group of effective 1-arylpyrazoles of the present invention is that wherein:

$R_1$ is CN;
$R_3$ is a haloalkyl radical;
$R_4$ is $NH_2$;
X is $C\text{—}R_{12}$;
$R_{11}$ and $R_{12}$ represent, independently of one another, a halogen atom; and
$R_{13}$ is a haloalkyl radical.

A most preferred compound is 5-amino-1-(2,6-dichloro-4-trifluoromethylphenyl)-4-trifluoromethylsulfinyl-3-cyanopyrazole, hereafter designated as compound (A).

Compounds of formula (I) may be prepared according to known processes, for example as described in International Patent Publications No. WO 87/3781, 93/6089, and 94/21606 as well as in European Patent Applications 295117, 403300, 385809 or 679650, German Patent Publication 19511269 and U.S. Pat. No. 5,232,940 and 5,236,938 or other processes according to the knowledge of a man skilled in the art of chemical synthesis.

The following examples are given to illustrate the invention but should not be considered as limiting it.

EXAMPLE 1

A sugar cane field is planted with parallel rows of sugar cane plants. When the plants are 1 node high, an aqueous suspension of Compound A is sprayed upon the said plants at a rate of 60 g/ha. Sugar plants are harvested when the plants have reached maturity, that is to say when the CCS is about 12 units. CCS means commercial cane sugar content. It is defined in the following way: CCS=pol in cane–[impurities in cane/2]; impurities in cane=brix in cane–pol in cane; brix in cane=brix in first expressed juice×[97-fibre]/100; pol in cane=pol in first expressed juice×[95-fibre]/100; these definitions may be found in "The Standard Laboratory Manual for Australian Sugar Mills, Vol 1, Principles and Practices" edited by the Bureau of Sugar Experiment Stations, in Brisbane, December 1984.

The sugar juices extracted from the said harvested plants have no natural dextran content.

Untreated plants are cultivated in a same manner, but without any treatment with Compound A. Pests including weevil borer infested the said plants. The CCS reached a maximum of 11 units. A decrease of one unit in CCS is a huge damage for farms which are able to produce more than 100 tons per hectare. Furthermore the decrease in CCS is mainly due to dextran replacing the sugar, this sugar having been converted into dextran inside the plants. This poor quality of sugar juices results in a lower price of the crop.

EXAMPLE 2

Example 1 is reproduced, except that the application of Compound A is made by spraying of 50 g/ha when the sugar plants have one node and 25 g/ha when the same plants have five nodes.

Similar results are obtained.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for improving and/or increasing the sugar content and/or preventing reduction of the sugar content of sugar plants in need thereof, which comprises treating said plants with an amount effective to improve and/or increase sugar content and/or to prevent reduction of sugar content in said plants of a compound of the formula:

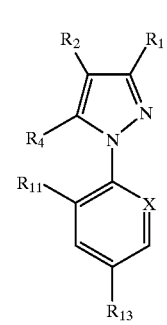

(I)

wherein:
$R_1$ is CN or methyl;
$R_2$ is $S(O)_nR_3$;
$R_3$ is alkyl or haloalkyl;
$R_4$ is a halogen atom or a member selected from the group consisting of $NR_5R_6$, $S(O)_mR_7$, $C(O)R_7$, $C(O)O\text{—}R_7$, alkyl, haloalkyl, $OR_8$ and $\text{—}N=C(R_9)(R_{10})$;
$R_5$ and $R_6$ independently represent a hydrogen atom or an alkyl, haloalkyl, C(O)alkyl, or alkoxycarbonyl radical; or $R_5$ and $R_6$ together form a divalent alkylene radical which is optionally interrupted by one or two divalent heteroatoms;

$R_7$ represents an alkyl or haloalkyl radical;

$R_8$ represents an alkyl or haloalkyl radical or a hydrogen atom;

$R_9$ represents an alkyl radical or hydrogen atom;

$R_{10}$ represents a phenyl or heteroaryl radical which is unsubstituted or substituted by one or more halogen atoms or a member selected from the group consisting of OH, —O-alkyl, —S-alkyl, cyano, and alkyl;

X represents a trivalent nitrogen atom or a C—$R_{12}$ radical, the other three valences of the carbon atom forming part of the aromatic ring;

$R_{11}$ and $R_{12}$ represent, independently of each other, a hydrogen or halogen atom;

$R_{13}$ represents a halogen atom or a haloalkyl, haloalkoxy, $S(O)_qCF_3$ or $SF_5$ group; and m, n and q represent, independently of one another, an integer equal to 0, 1, or 2;

provided that, when $R_1$ is methyl, then $R_3$ is haloalkyl, $R_4$ is $NH_2$, $R_{11}$ is Cl, $R_{13}$ is $CF_3$ and X is N; and wherein said compound of formula (I) is applied to the stalk of the plant.

2. A method according to claim 1, wherein the production of dextran in the sugar juices extracted from the treated sugar plants is decreased or prevented.

3. A method according to claim 1, wherein the compound of formula (I) is applied at a dose of from about 10 to about 200 g/ha.

4. A method according to claim 3, wherein the dose of compound of formula (I) applied is from about 20 to about 150 g/ha.

5. A method according to claim 4, wherein the dose of compound of formula (I) applied is from about 20 to about 100 g/ha.

6. A method according to claim 1, wherein $R_1$ is CN; $R_3$ is a haloalkyl radical; $R_4$ is $NH_2$; X is C—$R_{12}$; $R_{11}$ and $R_{12}$ represent, independently of each other, a halogen atom; and $R_{13}$ is a haloalkyl radical.

7. A method for improving and/or increasing the sugar content and/or preventing reduction of the sugar content of sugar plants in need thereof, which comprises treating said plants with an amount of the compound 5-amino-1-(2,6-dichloro-4-trifluoromethylphenyl)-4-trifluoromethyl-sulfinyl-3-cyanopyrazole effective to improve and/or increase sugar content and/or to prevent reduction of sugar content in said plants, wherein the compound is applied to the stalk of the plant.

8. A method according to claim 7, wherein the production of dextran in the sugar juices extracted from the treated sugar plants is decreased or prevented.

9. A method according to claim 7, wherein the compound is applied at a dose of from about 10 to about 200 g/ha.

10. A method according to claim 9, wherein the dose of compound applied is from about 20 to about 150 g/ha.

11. A method according to claim 10, wherein the dose of compound applied is from about 20 to about 100 g/ha.

12. A method for improving and/or increasing the sugar content and/or preventing reduction of the sugar content of sugar cane plants in need thereof which comprises treating said plants with an amount effective to improve and/or increase sugar content and/or to prevent reduction of sugar content in said plants of a compound of the formula:

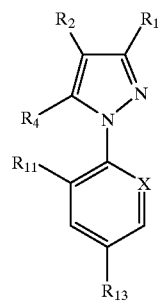

wherein:

$R_1$ is CN or methyl;

$R_2$ is $S(O)_nR_3$;

$R_3$ is alkyl or haloalkyl;

$R_4$ is a hydrogen or halogen atom or a member selected from the group consisting of $NR_5R_6$, $S(O)_mR_7$, $C(O)R_7$, $C(O)O$—$R_7$, alkyl, haloalkyl, $OR_8$ and —N=C($R_9$)($R_{10}$);

$R_5$ and $R_6$ independently represent a hydrogen atom or an alkyl, haloalkyl, C(O)alkyl, alkoxycarbonyl or $S(O)_rCF_3$ radical; or $R_5$ and $R_6$ together form a divalent alkylene radical which is optionally interrupted by one or two divalent heteroatoms;

$R_7$ represents an alkyl or haloalkyl radical;

$R_8$ represents an alkyl or haloalkyl radical or a hydrogen atom;

$R_9$ represents an alkyl radical or hydrogen atom;

$R_{10}$ represents a phenyl or heteroaryl radical which is unsubstituted or substituted by one or more halogen atoms or a member selected from the group consisting of OH, —O-alkyl, —S-alkyl, cyano, and alkyl;

X represents a trivalent nitrogen atom or a C—$R_{12}$ radical, the other three valences of the carbon atom forming part of the aromatic ring;

$R_{11}$ and $R_{12}$ represent, independently of each other, a hydrogen or halogen atom;

$R_{13}$ represents a halogen atom or a haloalkyl, haloalkoxy, $S(O)_qCF_3$ or $SF_5$ group;

m, n, q, and r represent, independently of one another, an integer equal to 0, 1, or 2;

provided that, when $R_1$ is methyl, then $R_3$ is haloalkyl, $R_4$ is $NH_2$, $R_{11}$ is Cl, $R_{13}$ is $CF_3$ and X is N; and wherein said compound of formula (I) is applied to the stalk of the plant when it has from one to five nodes.

13. A method for improving and/or increasing the sugar content and/or preventing reduction of the sugar content of sugar cane plants in need thereof, which comprises treating said plants with an amount of the compound 5-amino-1-(2,6-dichloro-4-trifluoromethylphenyl)-4-trifluoromethyl-sulfinyl-3-cyanopyrazole effective to improve and/or increase sugar content and/or to prevent reduction of sugar content in said plants, wherein the compound is applied to the stalk of the plant when it has from one to five nodes.

* * * * *